United States Patent [19]

Haak et al.

[11] Patent Number: 5,374,242

[45] Date of Patent: Dec. 20, 1994

[54] IONTOPHORETIC DELIVERY DEVICE AND POWER SUPPLY THEREFOR

[75] Inventors: Ronald P. Haak, San Jose, Calif.; Larry A. Mc Nichols; John D. Badzinski, both of Coon Rapids, Minn.

[73] Assignee: Alza Corporation, Palo Alto, Calif.

[21] Appl. No.: 164,663

[22] Filed: Dec. 7, 1993

Related U.S. Application Data

[63] Continuation of Ser. No. 802,080, Dec. 3, 1991, abandoned.

[51] Int. Cl.[5] ............................................. A61N 1/30
[52] U.S. Cl. ..................................... 604/20; 607/75; 607/115; 607/152
[58] Field of Search ................. 607/75, 115, 152, 153; 604/20, 21

[56] References Cited

U.S. PATENT DOCUMENTS

| | | | |
|---|---|---|---|
| 4,292,968 | 10/1981 | Ellis | 604/20 |
| 5,053,001 | 10/1991 | Keller et al. | 604/20 |

FOREIGN PATENT DOCUMENTS 8808729  11/1988  WIPO.

*Primary Examiner*—Lee S. Cohen
*Assistant Examiner*—Brian L. Casler
*Attorney, Agent, or Firm*—D. Byron Miller; Steven F. Stone; Edward L. Mandell

[57] ABSTRACT

An iontophoretic drug-delivery device incorporating a power supply which minimizes the cost of the batteries needed by operating the batteries in a series configuration at the start of delivery, when the patient's skin resistance is high, and by switching the batteries into a parallel configuration when skin resistance drops. An automatic switching circuit for achieving this transition is included.

33 Claims, 3 Drawing Sheets

IONTOPHORETIC DELIVERY DEVICE AND POWER SUPPLY THEREFOR

This is a continuation of Ser. No. 07/802,080 filed Dec. 3, 1991, now abandoned.

TECHNICAL FIELD

This invention relates to an iontophoretic device for transdermally or transmucosally delivering a beneficial agent to a patient. More particularly, the invention relates to an electrically powered iontophoretic delivery device having an improved power supply.

BACKGROUND ART

In the past, iontophoresis has been defined to be "the introduction, by means of electric current, of ions of soluble salts into the tissues of the body for therapeutic purposes." Iontophoretic devices have been used since the early part of this century for delivering agents in ionized form.

The iontophoresis process has been found to be useful in the transdermal administration of drugs including lidocaine hydrochloride, hydrocortisone, fluoride, penicillin, dexamethasone sodium phosphate, and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

Presently known iontophoretic devices use at least two electrodes, positioned in intimate contact with some portion of the skin of the body. A first electrode, called the active or donor electrode, delivers the ionic substance, medicament, drug precursor or drug into the body by iontophoresis. The second electrode, called the counter or return electrode, closes an electrical circuit including the body, the first electrode and a source of electrical energy, such as a battery. For example, if the ionic substance to be driven into the body is positively charged, the anode will be the active electrode and the cathode will serve as the counter electrode to complete the circuit. If the ionic substance to be delivered is negatively charged, the cathode will be the active electrode and the anode will be the counter electrode.

Alternatively, both the anode and cathode may be used to deliver drugs of opposite electrical charge into the body. In this situation, both electrodes are considered to be active or donor electrodes. For example, the anode can drive a positively charged ionic substance into the body, and the cathode can drive a negatively charged ionic substance into the body.

More recently, it has been determined that iontophoretic delivery devices can also be used to deliver an uncharged drug or agent into the body. This is accomplished by a process known as electroosmosis. Electroosmosis is the transdermal flux of a liquid solvent (e.g., the liquid solvent containing the uncharged drug or agent) that is induced by the presence of an electrical field imposed across the skin by the donor electrode. As used herein, the terms "iontophoresis" and "iontophoretic" refer to (1) the delivery of charged drugs or agents by electromigration, (2) the delivery of uncharged drugs or agents by electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

The terms "drug" and "beneficial agent" are used interchangeably and are intended to have their broadest interpretation, namely any therapeutically active substance that is delivered to a living organism to produce a desired, usually beneficial, effect. This includes therapeutic agents in all the major therapeutic areas including, but not limited to: anti-infectives, such as antibiotics and antiviral agents; analgesics, including fentanyl, sufentanil, buprenorphine and analgesic combinations; anesthetics; anorexics; antiarthritics; antiasthmatic agents; such as terbutaline; anticonvulsants; antidepressants; antidiabetic agents; antidiarrheals; antihistamines; antiinflammatory agents; antimigraine preparations; antimotion sickness preparations, such as scopalomine and ondansetron; antinauseants; antineoplastics; antiparkinsonism drugs; antipruritics; antipsychotics; antipyretics; antispasmodics, including gastrointestinal and urinary; antocholinergics; sympathomimetrics; xanthine derivatives; cardiovascular preparations, including calcium channel blockers such as nifedipine; beta blockers; beta-agonists, such as dobutamine and ritodrine; antiarythmics; antihypertensives, such as atenolol; ACE inhibitors, such as rinitidine; diuretics; vasodilators, including general, coronary, peripheral, and cerebral; central nervous system stimulants; cough and cold preparations; decongestants; diagnostics; hormones, such as parathyroid hormone; hypnotics; immunosuppressants; muscle relaxants; parasympatholytics; parasympathomimetrics; prostaglandins; proteins; peptides; psychostimulants; sedatives; and tranquilizers.

The invention is also useful in the controlled delivery of peptides, polypeptides, proteins and other macromolecules. These macromolecular substances typically have a molecular weight of at least 300 Daltons, and more typically have a molecular weight of 300–40,000 Daltons. Specific examples of peptides and proteins in this size range include, without limitation, the following: LHRH; LHRH analogs, such as buserelin, gonadorelin, napharelin and leuprolide; insulin; insulotropin; heparin; calcitonin; octreotide; endorphin; TRH; NT-36 (chemical name is N=[[(s)-4-oxo-2-azetidinyl]carbonyl]-L-histidyl-L-prolinamide); liprecin; pituitary hormones, such as HGH, HMG, HCG and desmopressin acetate; follicle luteoids; aANF; growth factors, such as growth factor releasing factor (GFRF or GHRH); bMSH; somatostatin; bradykinin; somatotropin; platelet-derived growth factor; asparaginase; bleomycin sulfate; chymopapain; cholecystokinin; chorionic gonadotropin; corticotropin (ACTH); erythropoietin; epoprostenol (platelet aggregation inhibitor); glucagon; hirulog; hyaluronidase; interferon; interleukin-1; interleukin-2; menotropins (urofollitropin (FSH) and LH); oxytocin; streptokinase; tissue plasminogen activator; vasopressin; desmopressin; ACTH analogs; ANP; ANP clearance inhibitors; angiotensin II antagonists; antidiuretic hormone agonists; antidiuretic hormone antagonists; bradykinin antagonists; CD-4; ceredase; CSFs; enkephalins; FAB fragments; IgE peptide suppressors; IGF-1; neurotrophic factors; colony stimulating factors; parathyroid hormone and agonists; parathyroid hormone antagonists; prostaglandin antagonists; pentigetide; protein C; protein S; renin inhibitors; thymosin alpha-1; thrombolytics; TNF; vaccines; vasopressin antagonist analogs; alpha-1 anti-trypsin (recombinant); and TGF-beta.

Existing iontophoresis devices generally require a reservoir or source of the agent, or a precursor of such agent, that is to be iontophoretically delivered or introduced into the body. Examples of such reservoirs or sources of, preferably ionized or ionizable, agent include a pouch as described in U.S. Pat. No. 4,250,878 issued to Jacobsen, or a pre-formed gel body as disclosed in U.S. Pat. No. 4,383,529 issued to Webster. Such reservoirs are electrically connected to the anode or the cathode of an iontophoresis device to provide a fixed or renewable source of one or more desired species.

Recently, a number of U.S. Patents have issued in the iontophoresis field, indicating a continuing interest in this mode of drug delivery. For example, Vernon et al U.S. Pat. No. 3,991,755, Jacobsen et al U.S. Pat. No. 4,141,359, Wilson U.S. Pat. No. 4,398,545, and Jacobsen U.S. Pat. No. 4,250,878 disclose examples of iontophoretic devices and some applications thereof.

The Dietz U.S. Pat. No. 3,215,139 discloses an iontophoretic delivery device for delivering fluoride to teeth. FIG. 12 of this patent shows a power supply consisting of batteries 102 and 104, either one of which is connectable into the circuit via switch 78. However, no provision is made for connecting both batteries simultaneously into the circuit.

The Sibalis U.S. Pat. No. 4,708,716 uses simply a series connection of a plurality of batteries as its power supply.

The Sibalis published European Patent application No. 88108314.1 uses a pair of batteries, either one of which is connectable into the circuit. However, like the Dietz patent, no provision is made to connect both batteries into the circuit at once.

As the above references illustrate, iontophoretic delivery devices for administering a wide range of drugs have become far more compact and inexpensive than the bulky, immobilizing apparatuses of the past. The advent of inexpensive miniaturized electronic circuitry and compact, high-energy batteries has meant that the entire device can be unobtrusively worn on the skin of the patient, who remains fully ambulatory and able to perform all normal activities. At the same time, the development of suitable chemistry and materials has made practical the iontophoretic administration of a much wider range of beneficial agents than was heretofore possible.

Nevertheless, some limitations still remain, restricting the wider application of this valuable technique. One such limitation is the cost of the iontophoretic device. In particular, the miniature batteries needed to power the iontophoretic device can comprise the most expensive element in the system. If it were possible to achieve a meaningful reduction in the cost of these batteries, iontophoresis could achieve a still further penetration of the highly competitive drug-delivery market.

The problem of reducing the cost of the batteries is complicated by the fact that the power-supply requirements are not constant during the utilization cycle of the iontophoretic device: When iontophoretic administration is begun, the patient's initial skin resistance is relatively high, requiring the supply to produce relatively high voltage. However, once iontophoretic delivery is established, the skin resistance drops, such that the voltage requirement may be less than one half the voltage required at the start.

Although various regulator circuits can be used to accommodate the varying voltage requirement, they reduce the efficiency of the apparatus and typically require that more battery capacity be provided, resulting in increased battery costs. A more cost-effective solution which makes optimal use of the batteries without wasting their energy in a regulator circuit is needed.

DESCRIPTION OF THE INVENTION

The present invention provides an iontophoretic beneficial agent delivery system at lower cost than heretofore.

The present invention provides an iontophoretic agent delivery system in which the power supply voltage can be varied to suit conditions of agent delivery.

The present invention provides an iontophoretic agent delivery system having a plurality of batteries as its source of power.

The present invention provides an iontophoretic agent delivery system having a plurality of voltage sources together with means to connect these sources in different arrangements to provide different supply voltages.

The present invention provides an iontophoretic agent delivery system with a plurality of batteries together with means for connecting the batteries in series or parallel.

The present invention provides an iontophoretic agent delivery system in which power supply voltage is automatically controlled in response to skin resistance of the patient.

An iontophoretic agent delivery system according to the present invention uses at least two electrical power sources, preferably in the form of high-energy batteries, together with a switch means which is selectively operable in either a first state, in which the power sources are connected in series, or in a second state, in which the power sources are connected in parallel. The series connection is appropriate for the initial phases of agent delivery, when skin resistance is high, while the parallel connection is suited for continuing operation when skin resistance has fallen.

Although operation of the switch can be manual, in accordance with a preferred embodiment of the invention, a switch control means in the form of an electronic circuit monitoring voltage at the agent delivery site is used to cause the transition of the switch from its first (series) state to its second (parallel) state.

BRIEF DESCRIPTION OF THE DRAWINGS

The above and other features, objects, and advantages of the present invention, together with the best mode known to the inventors for carrying out their invention, will become apparent from reading the, following description of the invention while studying the associated drawing, the various figures of which represent.

MODES FOR CARRYING OUT THE INVENTION

Figure 1:
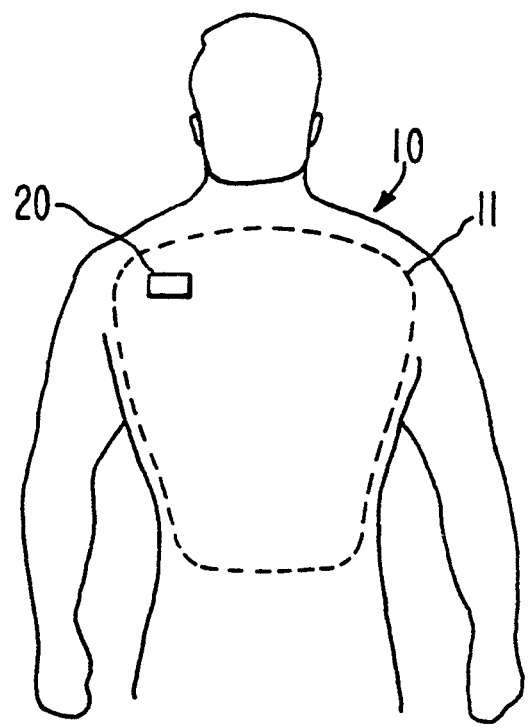
FIG. 1 is a perspective view showing the application of the invention to a human patient.

In FIG. 1 a human patient 10 is shown in posterior schematic perspective, with an iontophoretic agent delivery device 20 in place on the skin of the back, which is illustrated as that region of the body within the dotted outline 11. As fully explained in a copending U.S. patent application, Ser. No. 07/452,136, filed Dec. 14, 1989 and commonly assigned with the present application, the skin of the human back is a preferred site for the location of an iontophoretic agent delivery device.

Figure 2:
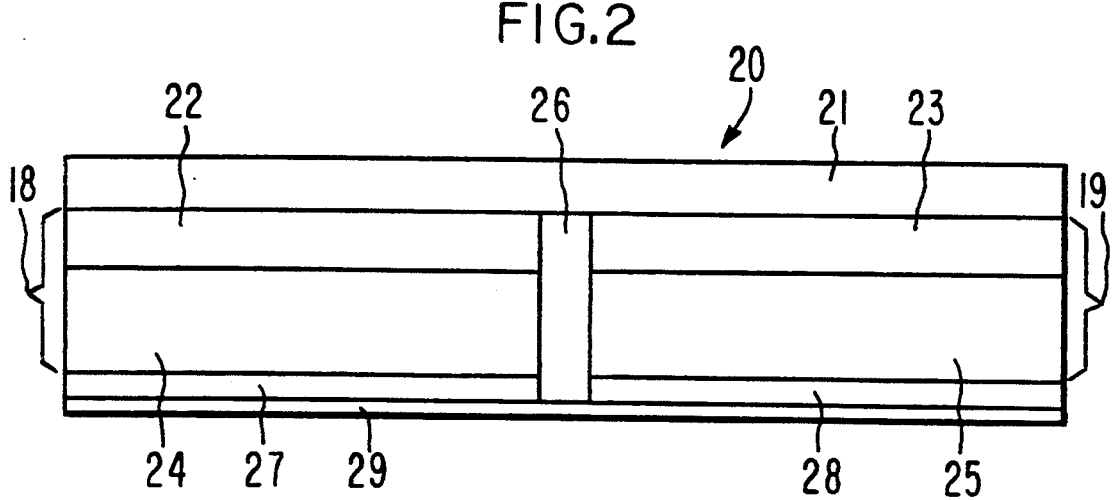
FIG. 2 is a schematic sectional view of an iontophoretic delivery device according to the present invention.

In FIG. 2 the device 20 of FIG. 1 is shown in a more detailed schematic sectional view. The top layer 21 of this device consists of a power supply, which will be described in much greater detail in the remaining portions of this description. The power supply includes a plurality of batteries, together with the associated control circuitry, switches, and connectors to supply voltage and current at appropriate levels over a period of time to device 20.

The remainder of device 20 is made up of a donor electrode assembly 18 and a return electrode assembly 19 separated both electrically and physically by an insulator 26, which may be a layer of an insulator material or which may be simply a void. Insulator 26 permits the incorporation of the donor electrode assembly and return electrode assembly 19 in the same unitary package by providing both chemical and electrical isolation of the two electrode assemblies.

Donor electrode assembly 18 includes a donor electrode 22 consisting typically of a metal foil or a polymer matrix loaded with a powdered conductor such as metal or carbon to render the matrix conductive. Donor electrode 22 serves to electrically couple the power supply of layer 21 to the underlying layer, which is a reservoir 24 containing, preferably, an ionizable supply of the beneficial agent or drug to be administered. Beneath reservoir 24 is an optional ion-conducting adhesive layer 27 for adhering device 20 to the skin of the patient, and a strippable release liner 29 which serves to protect adhesive layer 27 from contamination and which is removed just prior to application to the skin.

The structure of return electrode assembly 19 is very similar, and includes a return electrode 23 consisting of a metal foil or conductively loaded polymer matrix, a return reservoir 25 containing an electrolyte, and an optional ion-conducting adhesive layer 28 which is covered by liner 29. Each of the reservoirs 24 and 25 can be formed as a matrix of polymer or gel. The total area of skin contacted by electrode assemblies 18 and 19 typically ranges between 5 and 50 cm$^2$. As an alternative to the use of ion-conducting adhesive layers 27 and 28, device 20 may be adhered to the skin of a patient using any known adhesive overlay which is conventionally used in transdermal drug delivery.

In operation, device 20 initiates delivery of beneficial agent or drug by being adhered to an intact body surface of a patient, for example the skin of the patient as in FIG. 1. The power supply in layer 21 causes an electrical potential difference between donor electrode assembly 18 and return electrode assembly 19, while the body of the patient provides a conductive pathway therebetween. Under the influence of the potential difference between the donor and return electrode assemblies, ions of the beneficial agent are transported out of reservoir 24, through optional ion-conducting adhesive layer 27, and through the skin of the patient.

Figure 3:
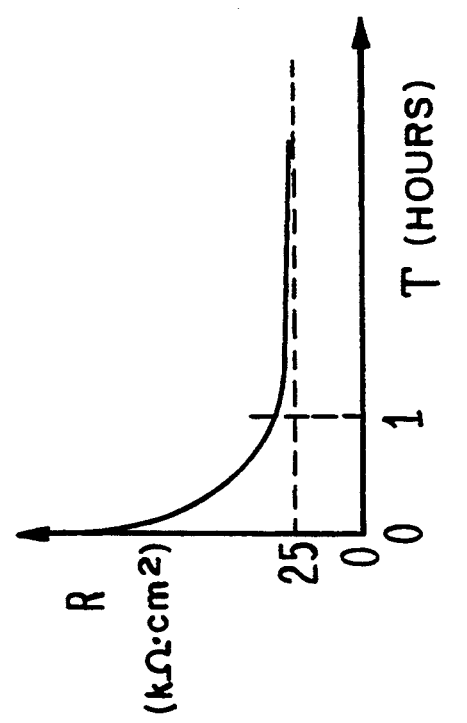
FIG. 3 is a graph illustrating the decline of patient skin resistance with time.

Upon first initiating agent delivery, the skin resistance of the patient is typically relatively high, whereas after a period of time, the skin resistance drops appreciably. FIG. 3 illustrates this characteristic graphically, showing that the decline of skin resistance R is substantially asymptotic to a steady state value. For a discharge rate of 0.1 ma/cm$^2$, this steady state value is typically on the order of 20 to 30 kohm-cm$^2$, while the initial value of skin resistance is several or many times as much.

In prior art devices, the voltage of the power supply was chosen large enough to overcome the high skin resistance present at the start of operation, while the capacity of the power supply in ampere-hours was chosen to equal the product of steady-state current and hours of usage. The result was that a sufficient number of batteries had to be provided such that when they were connected in series, the required initial voltage was produced. This meant that each of the batteries had to have sufficient capacity for the entire projected usage of the device. However, once operation had reached steady state, with the attendant drop in skin resistance, the prior art devices had excess battery voltage. In certain prior art devices, the number of batteries needed at steady state operation was one half or less of the number required for initiation. Accordingly, these prior-art devices were not very cost-effective because of the excessive number, and therefore the high cost, of batteries needed to operate them.

Figure 4:
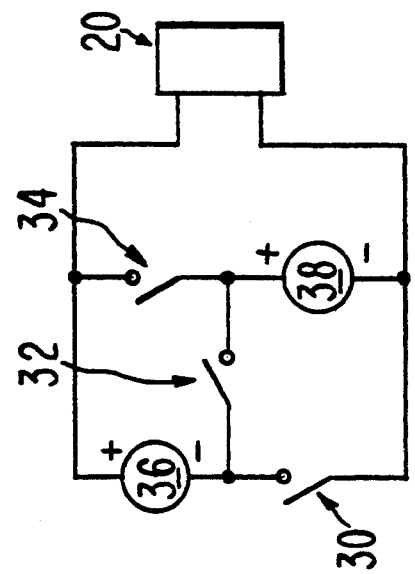
FIG. 4 is a block schematic diagram illustrating the novel power supply of the present invention.

In accordance with the present invention, FIG. 4 illustrates a simplified, manually operated power supply which permits more efficient use of batteries and results in significant cost savings when compared to the just-described prior art. In FIG. 4, three SPST (single pole, single throw) switches 30, 32, and 34 are shown interconnecting a pair of voltage sources 36 and 38 to agent delivery device 20 for the purpose of producing a voltage and current therein suitable for the delivery of beneficial agent. Switches 30–34 could in practice be separate sections of a more complex switch such as a DPDT (double-pole, double-throw) switch, a rotary switch, or any known electronic switch familiar to those skilled in the arts. Similarly, voltage sources 36 and 38 could each be a single battery, or could be made up of a plurality of such batteries, or could be realized in the form of any other known DC or AC voltage source.

The circuit arrangement of FIG. 4 is such that with switch 32 open as shown, the simultaneous closure of switches 30 and 34 places sources 36 and 38 in parallel circuit relationship with device 20. Such an arrangement is ideally suited to the steady-state operation of device 20 since each source need only deliver half of the current supplied to the load.

With switches 30 and 34 open, the closure of switch 32 places voltage sources 36 and 38 in series circuit relation. This configuration of the circuit is ideal for initiation of agent delivery, since the voltages of the sources are added to provide the higher voltage necessary to overcome high initial skin resistance the series circuit relation is also ideal for briefly increasing the rate of delivery of the beneficial agent during steady state operation. For example, if the agent being iontophoretically delivered to the patient is a pain-killer, the device can have a switch, manually operated by the patient, to momentarily switch to series circuit relation to increase the voltage and current supplied by the power source, and therefore increase the delivery of the drug during times of increased pain.

Accordingly, the use of a circuit arrangement such as that illustrated in FIG. 4 can reduce the battery capacity required to operate an agent delivery device by as much as a factor of two, since the capacity of the (one or more) batteries in each of voltage sources 36 and 38 need be only ½ as great as was required in the prior art series circuit described above. Furthermore, it will be obvious to those skilled in the art that the circuit arrangement of FIG. 4 can easily be modified to incorporate more than the illustrated two voltage sources 36 and 38. For example, three or more such sources could be used, together with additional switches to permit operation in series or parallel circuit relation as discussed above with respect to the two sources 36 and 38.

Although the manually operated power supply of FIG. 4 can be simply and cheaply implemented, its simplicity comes at the price of requiring too much operator attention in order to make the transition from series to parallel operation as agent delivery approaches the steady state condition. A power supply which can make this transition automatically at the appropriate time is preferred.

Figure 5:
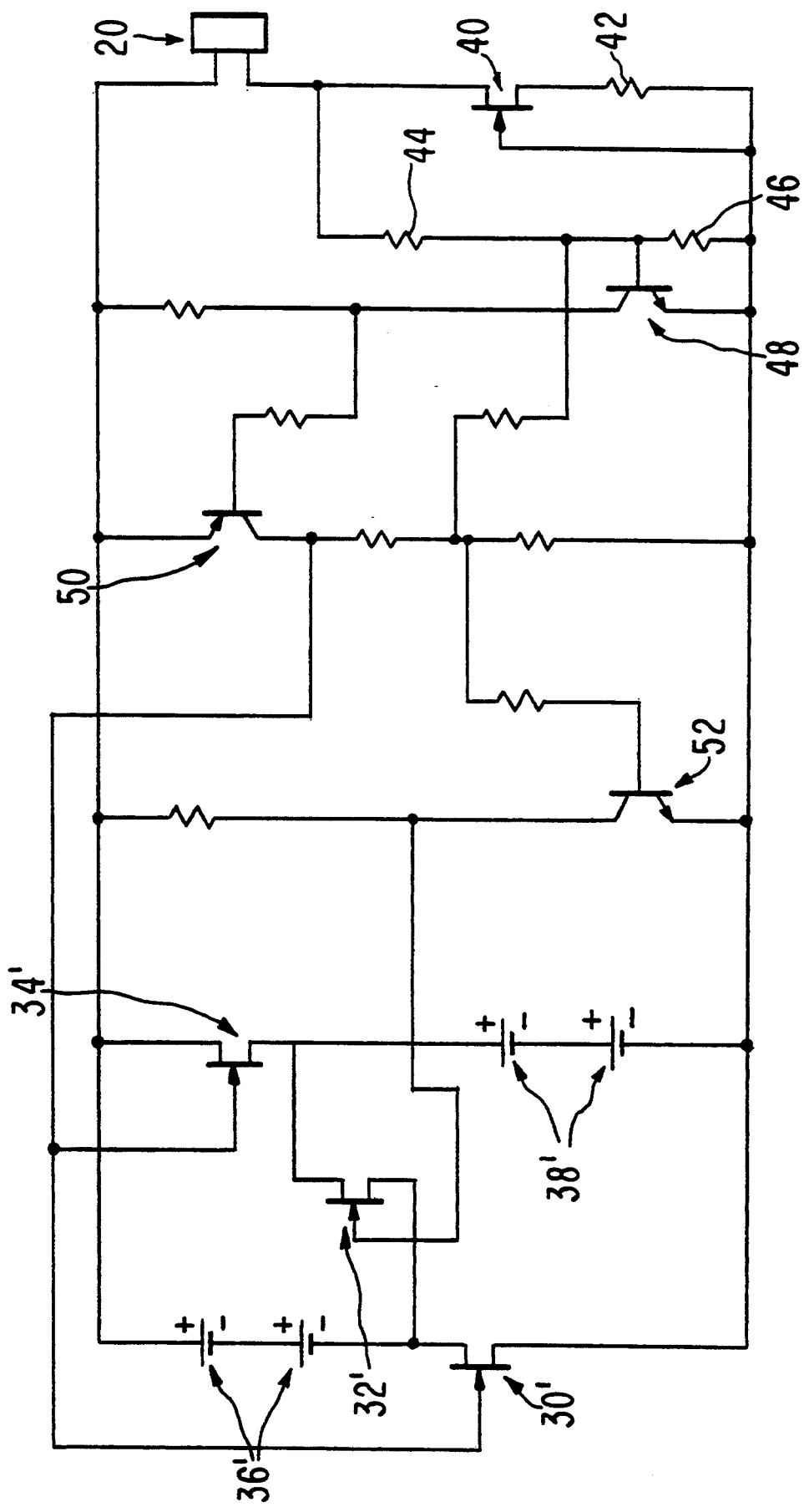
FIG. 5 is a detailed schematic diagram illustrating a preferred realization of the power supply of the present invention.

In FIG. 5, a power supply circuit for accomplishing automatic switching in accordance with the preferred embodiment of the present invention is illustrated. Although the power supply circuit of FIG. 5 is noticeably more complex than that of FIG. 4, many common elements such as voltage sources and switches are connected in the same circuit relationships and serve similar functions in the two circuits. For this reason, primed reference numerals have been used where appropriate.

Accordingly, the counterparts of voltage sources 36 and 38 of FIG. 4 are series-connected pairs of batteries, labeled 36' and 38' in FIG. 5. Similarly, the counterparts of manually operated switches 30, 32, and 34 are FETs (field-effect transistors) 30', 32', and 34'. In practice, the batteries 36' and 38' may be realized as, for example, type CR1220 ½ inch diameter lithium batteries producing a terminal voltage of approximately 2.8 volts. Such batteries are readily available from a number of sources, such as the Panasonic Corporation, Secaucus, N.J., U.S.A. and are widely distributed in wholesale and retail electronic parts channels. The FETs 30' and 32' may be realized as, for example, type VN10KM FETs, while FET 34' may be realized as, for example, a type VN67AK.

It will be understood that the portion of FIG. 5 thus far described matches the circuit of FIG. 4, with the exception that FETs 30'–34' are not manually switched, but switch in response to their gate voltage. That is, when the gate (arrowed terminal) of these devices is driven HIGH, the FET acts as a closed switch, while when the gate is driven LOW, the FET acts as an open switch.

The remainder of the circuit of FIG. 5 is devoted to providing the appropriate voltages to drive the gates of switching FETs 30'–34' to permit automatic switching of batteries 36' and 38' in response to the conditions present at iontophoretic agent delivery device 20. A JFET 40, together with its bias resistor 42 is connected in series with device 20 as a current regulator. JFET 40 may be, for example, a type 2N4220 device, while resistor 42 may have a value of approximately 3.3 kohms to establish a current of approximately 0.1 ma, for example.

Under initial conditions, when the patient's skin resistance is high, the voltage at the circuit node between device 20 and current regulator JFET 40 will be low, since most of the supplied voltage will appear across the terminals of device 20. The voltage on the just-mentioned node is sampled by a voltage divider made up of resistors 44 and 46, which may be, for example, 1 megohm and 56 kohm, respectively. The divided voltage at the junction of resistors 44 and 46 is used to bias the base of a transistor, for example, a type 2N2222 NPN switching transistor. Under initial conditions, transistor 48 will be OFF.

The HIGH collector voltage of transistor 48 biases the base of a transistor 50, for example, a type 2N2907 PNP switching transistor. Consequently, transistor 50 will also be OFF. Since the gates of both FETs 30' and 34' are biased from the (LOW) collector of transistor 50, both FETs 30' and 34' are OFF during initial startup conditions.

A transistor 52, for example, a type 2N2222 NPN switching transistor, is used to drive the gate of the remaining JFET 32' With transistor 50 OFF as noted above, transistor 52 sees a LOW bias voltage, and it is turned OFF, too. Accordingly, the collector terminal of transistor 52 goes HIGH, biasing FET 32' ON. Thus, under initial conditions, FET 32' is ON and FETs 30' and 34' are OFF, with the result that the batteries 36' and 38' are connected in series to supply maximum voltage to iontophoretic agent delivery device 20.

When operation of device 20 has continued for some time, such that skin resistance has dropped substantially in accordance with FIG. 3, the voltage at the circuit node between device 20 and current regulator transistor 40 will have risen. With sufficient increase of this voltage, the divided voltage used to bias the base of transistor 48 will be high enough to start to turn this transistor ON. The corresponding drop in the collector voltage of transistor 48 will similarly turn ON transistor 50, causing its collector to go HIGH, biasing transistor 52 ON. Under these conditions, FET 32' will be turned OFF, and FETs 30' and 34' will be turned ON, causing batteries 36' and 38' to be in parallel circuit connection with device 20 to supply steady-state current.

In view of the foregoing description of the operation of the power supply circuit of FIG. 5, it will be understood that one can view FET switches 30'–34' collectively as a bi-state switch having a first state in which the voltage sources (batteries 36' and 38') are connected in series, and a second state in which the voltage sources are connected in parallel. These two states are achieved, respectively, by turning FETs 30' and 34' OFF and turning FET 32' ON (first state), and by turning FETs 30' and 34' ON while turning FET 32' OFF (second state).

Similarly, it will be understood that transistors 48, 50, and 52 together with their circuit connections and bias resistors can be viewed as a switch control means for controlling the switch made up of FETs 30'–34'. The switch control means senses the voltage at the circuit node between device 20 and current-regulator transistor 40, compares this voltage with a voltage value pre-established by divider resistors 44 and 46, and causes the switch made up of FETs 30'–34' to transit from its first state (series connection) to its second state (parallel connection).

As an alternative to side-by-side alignment of the donor electrode assembly 18 and the return electrode assembly 19, shown in FIG. 2, these electrode assemblies can be concentrically aligned, with the return electrode assembly being centrally positioned and being surrounded by an annular donor electrode assembly.

Further, the electrode assembly positions can be interchanged, with an annular return electrode assembly surrounding a centrally positioned donor electrode assembly. Alignment of the two electrode assemblies may be circular, elliptical, rectangular, or any other consistent geometric configuration.

Although this invention has been described with some particularity in respect to embodiments thereof which, taken together, comprise the best mode known to the inventors for carrying out their invention, many changes could be made, and many alternative embodiments could thus be derived without departing from the scope of the invention. Consequently, the scope of the invention is to be determined only from the following claims.

We claim:

1. An iontophoretic delivery system for delivering a beneficial agent by iontophoresis through an intact body surface of a patient having an associated body surface electrical resistance, the system comprising:
    a first electrode means for containing a beneficial agent to be delivered and for contacting a body surface of a patient in agent-transmitting relation therewith;
    a second electrode means for contacting the body surface in ion-transmitting relation therewith at a location spaced apart from the first electrode means;
    first and second electrical power sources, each having a pair of terminals and each producing an electrical potential difference between its said pair of terminals; and
    bi-state switch means, coupled to said two power sources and said first and second electrode means, for selectively switching between: (1) a first state, in which said two power sources are connected in series circuit relation between said first and second electrode means, and (2) a second state, in which said two power sources are connected in parallel circuit relation between said first and second electrode means, where switching occurs in response to a change of electrical resistance of the patient's body surface.

2. The iontophoretic delivery system of claim 1 wherein said bi-state switch means comprises a manually operable switch.

3. The iontophoretic delivery system of claim 1 wherein at least one of said power sources comprises a DC source.

4. The iontophoretic delivery system of claim 1 wherein at least one of said power sources comprises a lithium battery.

5. The iontophoretic delivery system of claim 1 comprising a unitary iontophoretic delivery device incorporating said first and second electrode means.

6. The iontophoretic delivery system of claim 5 wherein said unitary iontophoretic delivery device further incorporates said two electrical power sources and said bi-state switch means.

7. The iontophoretic delivery system of claim 1, further including switch control means, coupled to said bi-state switch means and at least one of said first and second electrode means, for: (1) sensing the value of an electrical parameter present at least one of said first and second electrode means and associated with the delivery of electrical power from said power sources to said first and second electrode means, and (2) comparing the value of said sensed parameter with a pre-established value thereof, and (3) causing said bi-state switch means to transit between said first and second states, according to where the sensed parameter value lies in relation to the pre-established value.

8. The iontophoretic delivery system of claim 7 wherein said bi-state switch means comprises at least one field-effect transistor (FET).

9. The iontophoretic delivery system of claim 7, wherein said sensed parameter value is a voltage related to the resistance between said first and second electrode means.

10. The iontophoretic delivery system of claim 7, wherein said switch control means comprises a switching transistor coupled to at least one of said first and second electrode means and responding to the voltage thereat by causing said bi-state switch means to transit from said first state to said second state when said voltage exceeds said pre-established value.

11. The iontophoretic delivery system of claim 1, further including a constant current regulator coupled to said power sources and said first and second electrode means.

12. The iontophoretic delivery system of claim 11 wherein said constant current regulator comprises a JFET transistor.

13. The iontophoretic delivery system of claim 1, wherein said bi-state switch means comprises:
    a first electrical switch connected to a lower voltage terminal of said first power source and said first electrode means;
    a second electrical switch connected to the lower voltage terminal of said first power source and a higher voltage terminal of said second power source;
    a third electrical switch connected to said second electrode means and a higher voltage terminal of said second power source;
    where a higher voltage terminal of said first power source is connected to said second electrode means and a lower voltage terminal of said second power source is connected to said first electrode means; and
    where the first electrical switch and the third electrical switch are both open.

14. The iontophoretic delivery system of claim 1, wherein said bi-state switch means comprises:
    a first electrical switch connected to a lower voltage terminal of said first power source and said first electrode means;
    a second electrical switch connected to the lower voltage terminal of said first power source and a higher voltage terminal of said second power source;
    a third electrical switch connected to said second electrode means and a higher voltage terminal of said second power source;
    where a higher voltage terminal of said first power source is connected to said second electrode means and a lower voltage terminal of said second power source is connected to said first electrode means; and
    where the first electrical switch and the third electrical switch are both closed.

15. An iontophoretic delivery system for delivering a beneficial agent by iontophoresis through an intact body surface of a patient, said body surface having an electrical resistance, the system comprising:

a first electrode means for containing a beneficial agent to be delivered and for contacting the body surface of the patient in agent-transmitting relation therewith;

a second electrode means for contacting the body surface in ion-transmitting relation therewith at a location spaced apart from the first electrode means;

at least two electrical power sources, each producing an electrical potential difference; and bi-state switch means, coupled to said power sources and said first and second electrode means, for selectively switching between: (1) a first state, in which said two power sources are connected in series circuit relation between said first and second electrode means, and (2) a second state, in which said two power sources are connected in parallel circuit relation between said first and second electrode means, where switching occurs after the electrical resistance of the body surface drops from an initial electrical resistance level to a level substantially below said initial level.

16. The iontophoretic delivery system of claim 1 or 15, wherein the bi-state switch means comprises an automatically operable switch.

17. The iontophoretic delivery system of claim 1 or 15, wherein switching occurs when the body surface electrical resistance drops to a level below about 30 kohm-cm$^2$.

18. The iontophoretic delivery system of claim 1 or 15, wherein switching occurs when the body surface electrical resistance drops to a level of about 20 to 30 kohm-cm$^2$.

19. The iontophoretic delivery system of claim 15, further including switch control means, coupled to said bi-state switch means and at least one of said first and second electrode means, for (1) sensing a value of an electrical parameter present at at least one of said first and second electrode means and associated with the delivery of electrical power from said power sources to said first and second electrode means, and (2) comparing the value of said sensed parameter with a pre-established value thereof, and (3) causing said bi-state switch means to transit between said first and second states, according to where the sensed parameter value lies in relation to the pre-established value.

20. The iontophoretic delivery system of claim 15, wherein said bi-state switch means comprises at least one field effect transistor.

21. An iontophoretic delivery system for delivering a beneficial agent by iontophoresis through an intact body surface of a patient having an associated body surface electrical resistance, the system comprising:

a first electrode means for containing a beneficial agent to be delivered and for contacting a body surface of a patient in agent-transmitting relation therewith;

a second electrode means for contacting the body surface in ion-transmitting relation therewith at a location spaced apart from the first electrode means;

at least two electrical power sources, each having a pair of terminals and each producing an electrical potential difference between its said pair of terminals;

bi-state switch means, coupled to said two power sources and said first and second electrode means, for selectively switching between: (1) a first state in which said two power sources are connected in series circuit relation between said first and second electrode means, and (2) a second state in which said two power sources are connected in parallel circuit relation between said first and second electrode means; and switch control means, coupled to said bi-state switch means and at least one of said first and second electrode means, for sensing the voltage at one of said first and second electrode means and for causing said bi-state switch means to transit between its first state and its second state, according to where the sensed voltage lies in relation to a pre-established voltage value.

22. The iontophoretic delivery system of claim 21 wherein said bi-state switch means comprises a plurality of field-effect transistors (FETs).

23. The iontophoretic delivery system of claim 21, wherein said switch controls means comprises a switching transistor coupled to at least one of said first and second electrode means and responding to said sensed voltage thereat by causing said bi-state switch means to transit from said first state to said second state in response to said sensed voltage exceeding said pre-established voltage value.

24. The iontophoretic delivery system of claim 21, further including a constant current regulator coupled to said power sources and said first and second electrode means.

25. The iontophoretic delivery system of claim 24 wherein said constant current regulator comprises a JFET transistor.

26. A method of delivering a beneficial agent from an iontophoretic delivery system through a body surface of a patient, said body surface having an electrical resistance, the method comprising:

providing at least two electrical power sources to drive the delivery system;

electrically connecting the two power sources to first and second electrode means, the first electrode means containing a beneficial agent to be delivered, the first and second electrode means being for making electrical contact between the delivery system and the patient;

placing the first electrode means in agent-transmitting relation with the body surface;

placing the second electrode means in ion-transmitting relation with the body surface at a location spaced apart from the first is electrode means; and switching the two electrical power sources between (1) a first state in which the two power sources are connected in series circuit relation to the first and second electrode means when the body surface exhibits a high electrical resistance, and (2) a second state in which the two power sources are connected in parallel circuit relation to the first and second electrode means when the body surface exhibits an electrical resistance that is lower than the high resistance associated with the first state.

27. The method of claim 18, further comprising the steps of:

sensing an electrical parameter associated with the delivery of electrical power from said power sources to said first and second electrode means;

comparing the sensed value of the electrical parameter with a pre-established value thereof; and switching said power sources from said first state to said second state if said electrical parameter has a value above said pre-established value.

28. The method of claim 27, wherein said sensing step comprises sensing of the voltage at one of said first and second electrode means.

29. The method of claim 26, wherein the switching of the power sources occurs automatically.

30. The method of claim 26, wherein switching occurs when the body surface electrical resistance drops to a level below about 30 kohm-cm$^2$.

31. The method of claim 26, wherein switching occurs when the body surface electrical resistance drops to a level of about 20 to 30 kohm-cm$^2$.

32. The method of claim 26, further comprising:
sensing an electrical parameter associated with the delivery of electrical power from said power sources to said first and second electrode means;
comparing the sensed value of the electrical parameter with a pre-established value thereof; and
causing said power sources to transit between said first and second states according to where the sensed parameter value lies in relation to said pre-established value.

33. The method of claim 26, wherein the switching between the first and second states occurs with the two power sources connected between the first and second electrode means.

* * * * *